United States Patent [19]

Fey et al.

[11] Patent Number: 5,138,090
[45] Date of Patent: Aug. 11, 1992

[54] SUBSTITUTED BIPHENYLS

[75] Inventors: Peter Fey; Rolf Angerbauer; Walter Hübsch, all of Wuppertal; Thomas Philipps, Cologne; Hilmar Bischoff, Wuppertal; Peter Petzinna, Duesseldorf; Delf Schmidt, Wuppertal, all of Fed. Rep. of Germany

[73] Assignee: Bayer Aktiengesellschaft, Leverkusen, Fed. Rep. of Germany

[21] Appl. No.: 486,050

[22] Filed: Feb. 27, 1990

[30] Foreign Application Priority Data

Mar. 22, 1989 [DE] Fed. Rep. of Germany ....... 3909378

[51] Int. Cl.⁵ .............................................. C07C 69/76
[52] U.S. Cl. ........................................ 560/59; 562/469
[58] Field of Search ......................... 560/59; 562/469; 514/532

[56] References Cited

U.S. PATENT DOCUMENTS

| | | | |
|---|---|---|---|
| 3,655,743 | 4/1972 | Nickel et al. | 560/59 |
| 4,453,005 | 6/1984 | Belanger | 560/59 |
| 4,536,515 | 8/1985 | Belanger | 560/59 |
| 4,537,906 | 8/1985 | Belanger | 560/59 |
| 4,567,289 | 1/1986 | Willard | 560/59 |
| 4,992,429 | 2/1991 | Ullrich | 560/59 |
| 5,001,128 | 3/1991 | Neuenschwander | 560/59 |

FOREIGN PATENT DOCUMENTS

| | | |
|---|---|---|
| 0068038 | 1/1983 | European Pat. Off. . |
| 0232997 | 8/1987 | European Pat. Off. . |
| 0344602 | 12/1989 | European Pat. Off. . |
| 8905639 | 6/1989 | World Int. Prop. O. . |

OTHER PUBLICATIONS

Lynch P. et al. Tetrahedron, Letters vol. 28 (13) pp. 1385-1388 1987.

Primary Examiner—Paul J. Killos
Attorney, Agent, or Firm—Sprung Horn Kramer & Woods

[57] ABSTRACT

Substituted biphenyls can be prepared by reduction of appropriate ketones and, if appropriate, subsequent hydrolysis, cyclization, hydrogenation and separation of isomers. The substituted biphenyls can be used as active compounds in medicaments.

7 Claims, No Drawings

SUBSTITUTED BIPHENYLS

The invention relates to new substituted biphenyls, to intermediate compounds for their preparation, and to their preparation and their use in medicaments.

It is known that lactone derivatives isolated from fungal cultures are inhibitors of 3-hydroxy-3-methyl-glutaryl-coenzyme A reductase (HMG-CoA reductase) [Mevinolin EP-A 22,478; U.S. Pat. No. 4,231,938]. Moreover, certain indole derivatives, pyrazole derivatives, biphenyl and phenyl derivatives are also inhibitors of HMG-CoA. reductase (EP-A 1,114,027; US Patent 4,613,610; U.S. Pat. No. 4,772,626; EP-A1 0,282,217 and EP-A1 0,283,217].

New substituted biphenyls of the general formula

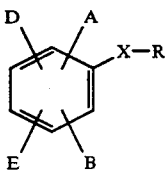

(I)

in which

A—represents a 3- to 7-membered heterocycle, which may contain up to 4 heteroatoms from the series comprising sulphur, oxygen or nitrogen and which is optionally monosubstituted to pentasubstituted by identical or different substituents from the series comprising halogen, trifluoromethyl, trifluoromethylthio, trifluoromethoxy, straight-chain or branched alkyl, alkylthio, alkylsulphonyl, alkoxy or alkoxycarbonyl each having up to 8 carbon atoms, by aryl, arylthio or arylsulphonyl having 6 to 10 carbon atoms or by a group of the formula —$NR^1R^2$, wherein $R^1$ and $R^2$ are identical or different and denote hydrogen, aryl or arylsulphonyl having 6 to 10 carbon atoms, straight-chain or branched alkyl or alkylsulphonyl having up to 8 carbon atoms, the lastmentioned radicals optionally being substituted by aryl having 6 to 10 carbon atoms, or denote a group of the formula —$COR^3$ wherein $R^3$—denotes straight-chain or branched alkyl or alkoxy having up to 8 carbon atoms, or phenyl, represents aryl having 6 to 10 carbon atoms, which is optionally monosubstituted to pentasubstituted by identical or different substituents from the series comprising straight-chain or branched alkyl, alkylthio, alkylsulphonyl, alkoxy or alkoxycarbonyl each having up to 10 carbon atoms, which may in turn be substituted by hydroxyl, alkoxy having up to 6 carbon atoms, phenyl or by a group of the formula —$NR^1R^2$, or is substituted by aryl, aryloxy, arylthio or arylsulphonyl having 6 to 10 carbon atoms, or by halogen, nitro, cyano, trifluoromethyl, trifluoromethoxy, trifluoromethylthio, benzyloxy or a group of the formula —$NR^1R^2$, wherein $R^1$ and $R^2$ have the abovementioned meanings, B—represents cycloalkyl having 3 to 8 carbon atoms, represents straight-chain or branched alkyl having up to 12 carbon atoms, which is optionally substituted by halogen, cyano, azido, trifluoromethyl, trifluoromethoxy, trifluoromethylthio, trifluoromethylsulphonyl, alkoxy having up to 10 carbon atoms, aryl, aryloxy or arylthio having 6 to 10 carbon atoms or by a 5- to 7-membered heterocycle having up to 4 heteroatoms from the series comprising sulphur, oxygen or nitrogen, where this heterocycle and the aryl radicals may optionally be monosubstituted to trisubstituted by identical or different substituents from the series comprising halogen, cyano, trifluoromethyl, trifluoromethoxy, straight-chain or branched alkyl, alkoxy, alkylthio or alkylsulphonyl each having up to 8 carbon atoms, or is substituted by a group of the formula —$NR^1R^2$ or —$COR^3$, wherein $R^1$, $R^2$ and $R^3$ have the abovementioned meanings, represents aryl having 6 to 10 carbon atoms, which is optionally substituted by halogen, cyano, nitro, trifluoromethyl, straight-chain or branched alkyl, alkoxy or alkoxycarbonyl each having up to 8 carbon atoms, or amino, D and E are identical or different and have the abovementioned meaning of A and are identical or different to this, or represent cycloalkyl having 3 to 6 carbon atoms, represent straight-chain or branched alkyl or alkenyl each having up to 12 carbon atoms, which is optionally substituted by halogen, azido, aryl having 6 to 10 carbon atoms, by a 5- to 7-membered heterocycle having up to 4 heteroatoms from the series comprising nitrogen, oxygen or sulphur, or by a group of the formula —$NR^1R^2$, —$OR^4$, —$COR^5$ or $S(O)_n$—$R^6$, wherein $R^1$ and $R^2$ have the abovementioned meanings, $R^4$—denotes hydrogen or denotes straight-chain or branched alkyl having up to 10 carbon atoms, which is optionally substituted by hydroxyl, halogen or aryl having 6 to 10 carbon atoms, which may in turn be substituted by halogen, cyano, nitro, hydroxyl, straight-chain or branched alkyl, alkoxy or alkoxycarbonyl each having up to 8 carbon atoms, or amino, denotes cycloalkyl having 3 to 8 carbon atoms or denotes aryl having 6 to 10 carbon atoms which may in turn be substituted by halogen, cyano, nitro or amino, or denotes a group of the formula —$COR^7$, wherein $R^7$—denotes straight-chain or branched alkyl having up to 8 carbon atoms, aryl having 6 to 10 carbon atoms or the group —$NR^1R^2$, $R^5$—denotes hydrogen or straight-chain or branched alkyl having up to 10 carbon atoms, which is optionally substituted by hydroxyl, phenyl, halogen or cyano, denotes aryl having 6 to 10 carbon atoms or a 5- to 7-membered heterocycle having up to 4 heteroatoms from the series comprising sulphur, nitrogen or oxygen, which may in turn be substituted by halogen, amino, hydroxyl, nitro or cyano, or denotes a group of the formula —$NR^1R^2$ or —$OR^4$, wherein $R^1$, $R^2$ and $R^4$ have the abovementioned meanings, n—denotes a number 0, 1 or 2, $R^5$—denotes straight-chain or branched alkyl having up to 10 carbon atoms, which may be substituted by halogen, hydroxyl or phenyl, denotes aryl having 6 to 10 carbon atoms, which may be substituted by halogen, hydroxyl, cyano, nitro or amino, X—represents a group of the formula —CH$_2$—CH$_2$— or —CH=CH—, and R—represents a group of the formula

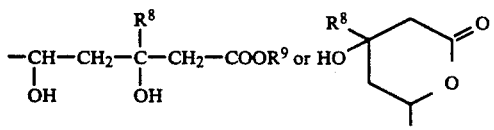

wherein $R^8$—denotes hydrogen or straight-chain or branched alkyl having up to 10 carbon atoms, and $R^9$—denotes hydrogen or straight-chain or branched alkyl having up to 10 carbon atoms, which may be substituted by phenyl, or denotes aryl having 6 to 10 carbon atoms, or a cation, or D—represents the group —X—R, where X and R have the abovementioned meanings, and their salts have now been found.

If $R^9$ forms an ester radical with the carboxyl group, a physiologically tolerable ester radical, which is easily hydrolyzed in vivo to give a free carboxyl group and a corresponding physiologically tolerable alcohol, is preferably meant by this. These include, for example, alkyl esters (C$_1$ to C$_6$) and aralkyl esters (C$_7$ to C$_{10}$), preferably (C$_1$–C$_4$)-alkyl esters and benzyl esters. Moreover, the following ester radicals may be mentioned: methyl esters, ethyl esters, propyl esters and benzyl esters.

If $R^9$ represents a cation, a physiologically tolerable metal cation or ammonium cation is preferably meant. Those preferred in this connection are alkali metal or alkaline earth metal cations such as, for example, sodium, potassium, magnesium or calcium cations, and also aluminum or ammonium cations, as well as nontoxic substituted ammonium cations of amines such as (C$_1$–C$_4$)-dialkylamines, (C$_1$–C$_4$)-trialkylamines, procaine, dibenzylamine, N,N'-dibenzylethylenediamine, N-benzyl-β-phenylethylamine, N-methylmorpholine or N-ethylmorpholine, 1-ephenamine, dihydroabietylamine, N,N'-bis-dihydroabiety-lethylenediamine, N-lower alkylpiperidine and other amines which can be used for the formation of salts.

Surprisingly, the substituted biphenyls according to the invention show a superior inhibitory action on HMG-CoA reductase (3-hydroxy-3-methyl-glutaryl-coenzyme A reductase).

Preferred compounds of the general formula (I) are those in which

A—represents thienyl, furyl, pyridyl, pyrimidyl or pyrazinyl, which is optionally monosubstituted to tetrasubstituted by identical or different substituents from the series comprising fluorine, chlorine, bromine, straight-chain or branched alkyl, alkoxy or alkoxycarbonyl each having up to 6 carbon atoms or phenyl, represents phenyl or naphthyl, which is optionally monosubstituted to tetrasubstituted by identical or different substituents from the series comprising straight-chain or branched alkyl, alkoxy or alkoxycarbonyl each having up to 8 carbon atoms, which may in turn be substituted by hydroxyl, alkoxy having up to 4 carbon atoms or phenyl, or is substituted by phenyl, phenyloxy, fluorine, chlorine, bromine, nitro, cyano, trifluoromethyl or benzyloxy, B—represents cyclopropyl, cyclobutyl, cyclopentyl or cyclohexyl, represents straight-chain or branched alkyl having up to 10 carbon atoms, which is optionally substituted by fluorine, chlorine, bromine, trifluoromethyl, alkoxy having up to 8 carbon atoms, or is substituted by phenyl or phenoxy, which may in turn be monosubstituted or disubstituted by identical or different substituents from the series comprising fluorine, chlorine, bromine, cyano, trifluoromethyl, trifluoromethoxy, straight-chain or branched alkyl or alkoxy each having up to 6 carbon atoms, or represents phenyl, which is optionally substituted by fluorine, chlorine, bromine, cyano, nitro, trifluoromethyl, straight-chain or branched alkyl, alkoxy or alkoxycarbonyl each having up to 6 carbon atoms, or amino, D and E are identical or different and have the abovementioned meaning of A and are identical or different to this, or represent cyclopropyl, cyclobutyl, cyclopentyl or cyclohexyl, represent straight-chain or branched alkyl having up to 10 carbon atoms, which is optionally substituted by fluorine, chlorine, bromine or phenyl, or substituted by a group of the formula —OR$^4$ or —COR$^5$, wherein $R^4$—denotes hydrogen or denotes straight-chain or branched alkyl having up to 8 carbon atoms, which is optionally substituted by hydroxyl, fluorine, chlorine, bromine, or by phenyl which may in turn be substituted by fluorine, chlorine, bromine, cyano, nitro, hydroxyl or straight-chain or branched alkyl having up to 6 carbon atoms, denotes phenyl, which in turn may be substituted by fluorine, chlorine, bromine, cyano, nitro or amino, or denotes a group of the formula —COR$^7$, wherein $R^7$—denotes straight-chain or branched alkyl having up to 6 carbon atoms or phenyl, $R^5$—denotes hydrogen, straight-chain or branched alkyl having up to 8 carbon atoms, denotes phenyl, which may in turn be substituted by fluorine, chlorine, bromine, amino, hydroxyl, nitro or cyano, or denotes a group of the formula —OR$^4$, wherein $R^4$ has the abovementioned meaning, X—represents a group of the formula —CH$_2$—CH$_2$— or —CH=CH— and R—represents a group of the formula

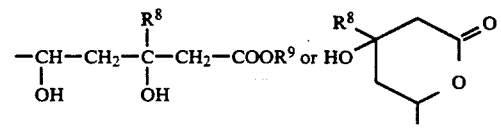

wherein

R[8]—denotes hydrogen or straight-chain or branched alkyl having up to 8 carbon atoms and R[9]—denotes hydrogen or straight-chain or branched alkyl having up to 8 carbon atoms, or benzyl, or denotes phenyl or a cation, or D—represents the group of the formula —X—R, wherein X and R have the abovementioned meanings, and their salts.

Particularly preferred compounds of the general formula (I) are those in which

A—represents phenyl, which is optionally monosubstituted to trisubstituted by identical or different substituents from the series comprising straight-chain or branched alkyl having up to 6 carbon atoms, fluorine, chlorine, nitro, cyano or trifluoromethyl, B—represents cyclopropyl, cyclobutyl, cyclopentyl or cyclohexyl, represents straight-chain or branched alkyl having up to 8 carbon atoms, represents phenyl which is substituted by fluorine, chlorine, or nitro, D and E are identical or different and have the abovementioned meaning of A and are identical or different to this, or represent cyclopropyl, cyclopentyl or cyclohexyl, represent straight-chain or branched alkyl having up to 8 carbon atoms, which is optionally substituted by fluorine, chlorine or phenyl, or is substituted by a group of the formula —OR[4], wherein R[4]—denotes hydrogen or denotes straight-chain or branched alkyl having up to 6 carbon atoms, which is optionally substituted by hydroxyl or phenyl, denotes a group of the formula —COR[7], wherein R[7]—denotes straight-chain or branched alkyl having up to 4 carbon atoms or phenyl, X—represents a group —CH=CH—, and R—represents a group of the formula

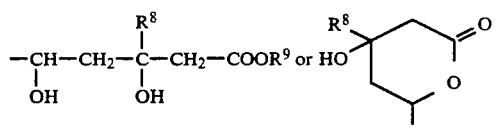

wherein

R[8]—denotes hydrogen, methyl, ethyl, propyl, isopropyl, butyl, isobutyl or tert.butyl and R[9]—denotes hydrogen, methyl, ethyl, propyl, isopropyl, butyl, isobutyl, tert.butyl or benzyl, or denotes a sodium, potassium, calcium, magnesium or ammonium ion or D—represents a group of the formula —X—R, wherein X and R have the abovementioned meanings, and their salts.

The substituted biphenyls of the general formula (I) according to the invention have a number of asymmetric carbon atoms and can therefore exist in various stereochemical forms. The invention relates both to the individual isomers and to their mixtures.

Depending on the meaning of the group X or the radical R, different stereoisomers result, which it is intended to illustrate in more detail in the following:

a) if the group —X— represents a group of the formula —CH=CH—, the compounds according to the invention can exist in two stereoisomeric forms which can have the E configuration (II) or Z configuration (III) at the double bond:

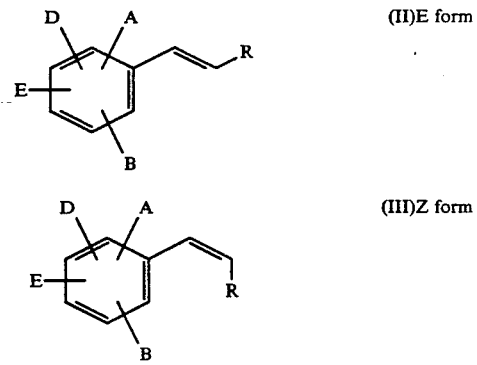

(A, B, D, E and R have the abovementioned meanings).

Preferred compounds of the general formula (I) are those which have the E configuration (II).

b) If the radical —R— represents a group of the formula

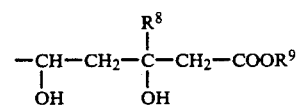

the compounds of the general formula (I) have at least two asymmetric carbon atoms, namely the two carbon atoms to which the hydroxyl groups are bonded. Depending on the relative position of these hydroxyl groups to one another, the compounds according to the invention can exist in the erythro configuration (IV) or in the threo configuration (V).

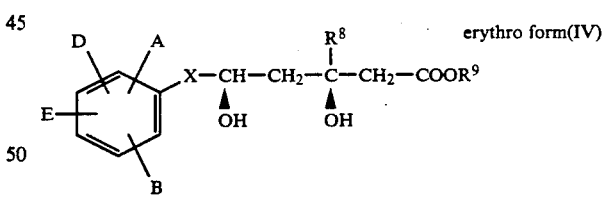

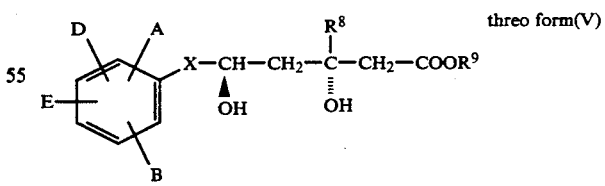

Two enantiomers in each case again exist of the compounds in the erythro and in the threo configuration, namely the 3R,5S isomer or the 3S,5R isomer (erythro form) and the 3R,5R isomer and 3S,5S isomer (threo form).

The isomers having the erythro configuration are preferred in this case, particularly preferably the 3R,5S isomer and the 3R,5S-3S,5R racemate.

c) If the radical —R— represents a group of the formula

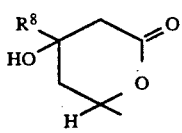

the substituted biphenyls have at least two asymmetric carbon atoms, namely the carbon atom to which the hydroxyl group is bonded and the carbon atom to which the radical of the general formula

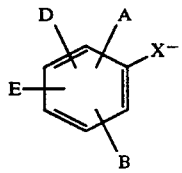

is bonded. Depending on the position of the hydroxyl group to the free valency on the lactone ring, the substituted biphenyls can exist as cis lactones (VI) or as trans lactones (VII)

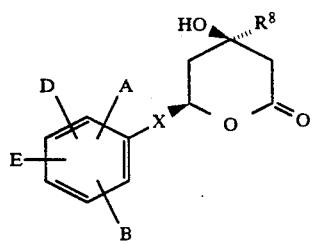
cis lactone (VI)

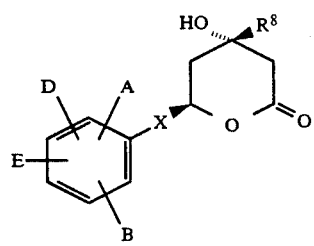
trans lactone (VII)

Two isomers in each case again exist of the cis lactone and the trans lactone, namely the 4R,6R isomer or the 4S,6S isomer (cis lactone), and the 4R,6S isomer or 4S,6R isomer (trans lactone). Preferred isomers are the trans lactones. The 4R,6S isomer (trans) and the 4R,6S-4S,6R-racemate is particularly preferred in this case.

Examples of the substituted biphenyls which may be mentioned are the following isomeric forms:

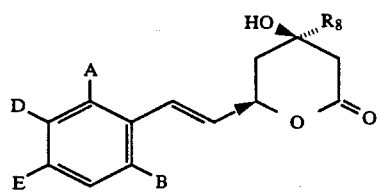

-continued

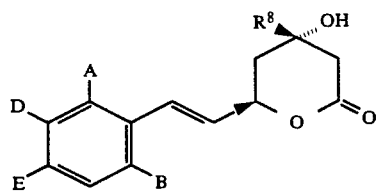

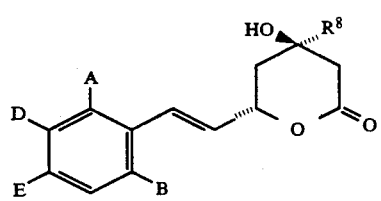

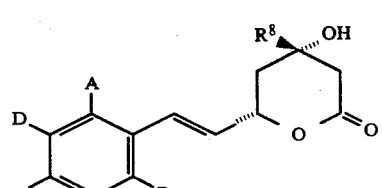

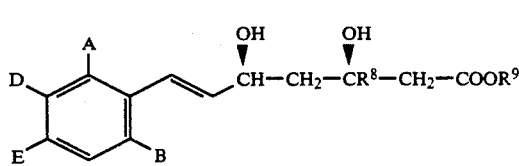

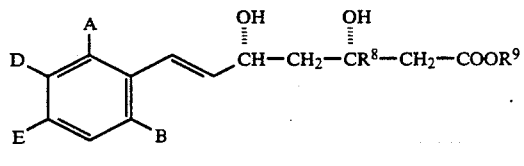

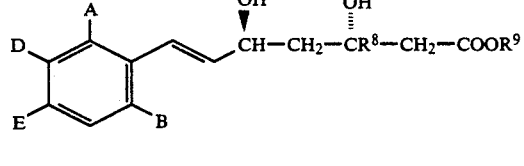

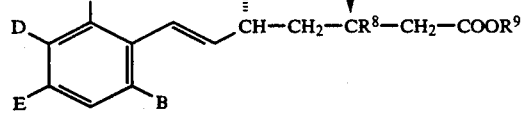

In addition, a process for the preparation of the substituted biphenyls of the general formula (I)

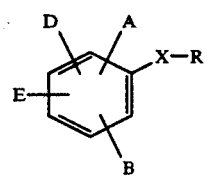

in which
A, B, D, E, X and R have the abovementioned meanings, has been found, which is characterized in that ketones of the general formula (VIII)

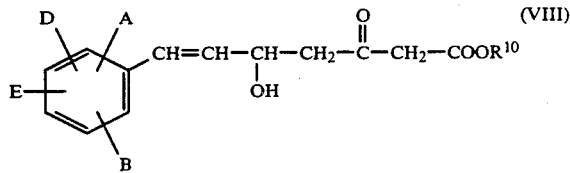

in which

A, B, D and E have the abovementioned meanings, and

R[10]—represents alkyl, are reduced, in the case of the preparation of the acids, the esters are hydrolyzed, in the case of the preparation of the lactones, the carboxylic acids are cyclized, in the case of the preparation of the salts, either the esters or the lactones are hydrolyzed, in the case of the preparation of the ethylene compounds (X=—CH$_2$—CH$_2$—), the ethene compounds (X=—CH=CH—) are hydrogenated by customary methods, and, if appropriate, isomers are separated.

The process according to the invention can e illustrated by the following equation:

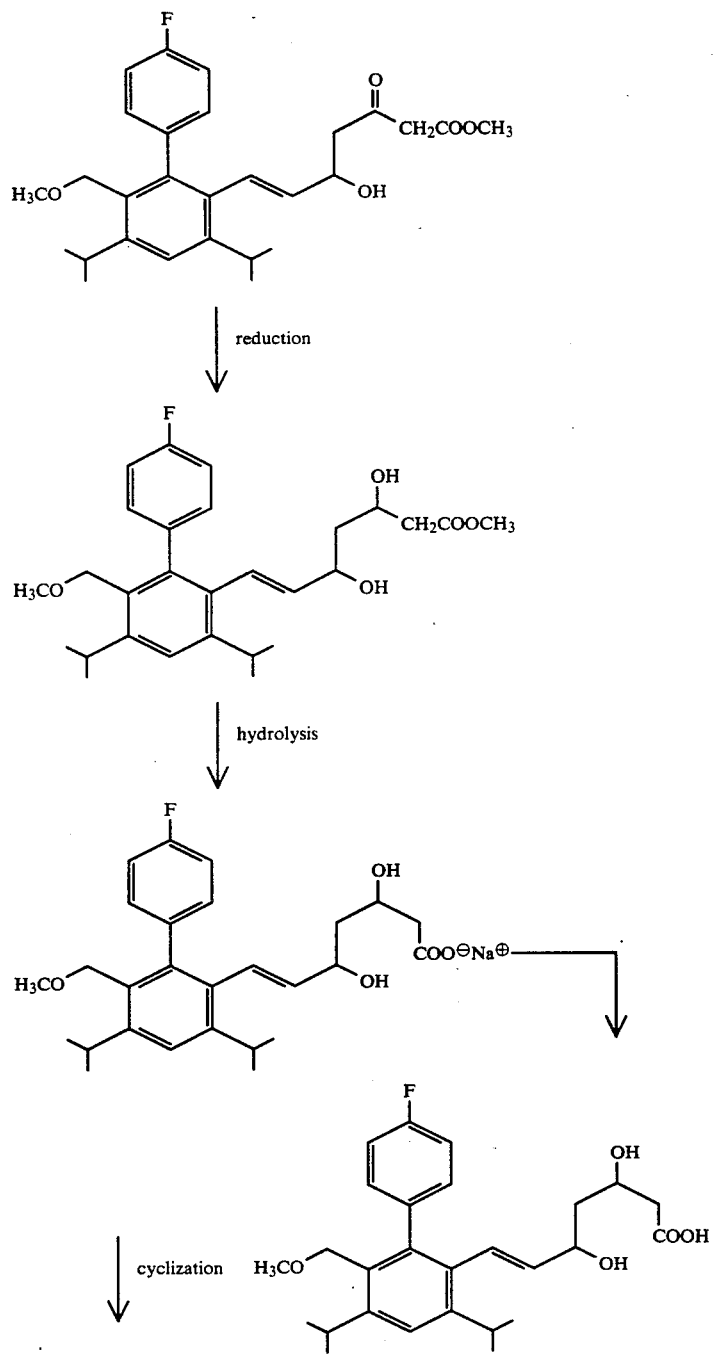

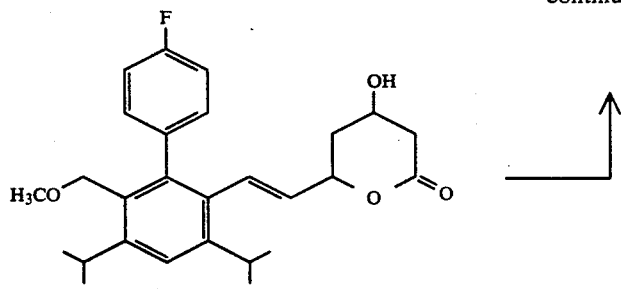

The reduction can be carried out using the customary reducing agents, preferably using those which are suitable for the reduction of ketones to give hydroxyl compounds. Reduction using metal hydrides or complex metal hydrides in inert solvents is particularly suitable in this connection, if appropriate in the presence of a trialkylborane. Reduction is preferably carried out using complex metal hydrides such as, for example, lithium borohydride, sodium borohydride, potassium borohydride, zinc borohydride, lithium trialkylborohydrides, sodium trialkylborohydrides, sodium cyanoborohydride or lithium aluminum hydride Reduction using sodium borohydride is very particularly preferred, carried out in the presence of triethylborane.

Suitable solvents in this connection are the customary organic solvents which do not change under the reaction conditions. These preferably include ethers such as, for example, diethyl ether, dioxane, tetrahydrofuran or dimethoxyethane, or halogenated hydrocarbons such as, for example, dichloromethane, trichloromethane, tetrachloromethane, 1,2-dichloroethane, or hydrocarbons such as, for example, benzene, toluene or xylene. It is also possible to employ mixtures of the solvents mentioned.

The reduction of the ketone group to the hydroxyl group is particularly preferably carried out under conditions in which the other functional groups such as, for example, the alkoxycarbonyl group are not changed. For this purpose, the use of sodium borohydride as a reducing agent, in the presence of triethylborane in inert solvents such as, for example, ethers, is particularly suitable.

The reduction is in general carried out in a temperature range from $-80°$ C. to $+30°$ C., preferably from $-78°$ C. to $0°$ C.

The process according to the invention is in general carried out at normal pressure. However, it is also possible to carry out the process at reduced pressure or at elevated pressure (for example in a range from 0.5 to 5 bar).

In general, the reducing agent is employed in an amount from 1 to 2 moles, preferably from 1 to 1.5 moles relative to 1 mole of the keto compound Under the abovementioned reaction conditions the carbonyl group is in general reduced to the hydroxyl group without reduction of the double bond to a single bond taking place.

In order to prepare compounds of the general formula (I), in which X represents an ethylene grouping, the reduction of the ketones (VIII) can be carried out under those conditions under which both the carbonyl group and the double bond are reduced.

Moreover, it is also possible to carry out the reduction of the carbonyl group and the reduction of the double bond in two separate steps.

The carboxylic acids in the context of the general formula (I) correspond to the formula (Ia)

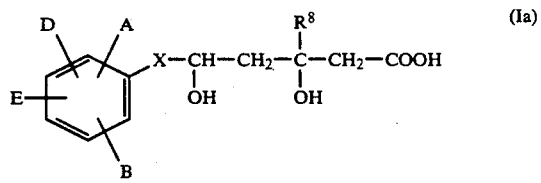

in which

A, B, D, E and $R^8$ have the abovementioned meanings.

The carboxylic acid esters in the context of the general formula (I) correspond to the formula (Ib)

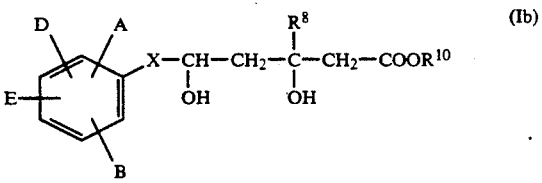

in which

A, B, D, E and $R^8$ have the abovementioned meanings, and $R^{10}$—represents alkyl.

The salts of the compounds according to the invention in the context of the general formula (I) correspond to the formula (Ic)

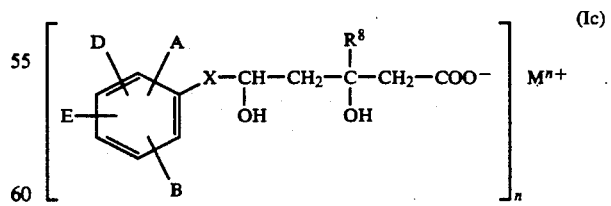

in which

A, B, D, E and $R^8$ have the abovementioned meanings, and $M^{n+}$ represents a cation, where n indicates the valency.

The lactones in the context of the general formula (I) correspond to the formula (Id)

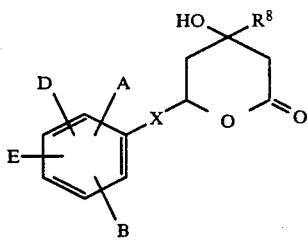

(Id)

in which

A, B, D, E and $R^8$ have the abovementioned meanings,

In order to prepare the carboxylic acids of the general formula (Ia) according to the invention, the carboxylic acid esters of the general formula (Ib) or the lactones of the general formula (Id) are in general hydrolyzed by customary methods. Hydrolysis is in general carried out by treating the esters or the lactones with customary bases in inert solvents, whereupon the salts of the general formula (Ic) are in general first formed, which can then be converted in a second step into the free acids of the general formula (Ia) by treating with acid.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogencarbonate, or alkali metal alkoxides such as sodium ethoxide, sodium methoxide, potassium methoxide, potassium ethoxide or potassium tert.butoxide. Sodium hydroxide or potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount from 1 to 3 moles, preferably from 1 to 1.5 moles relative to 1 mole of the ester or the lactone. Molar amounts of the reactants are particularly preferably used.

When carrying out the reaction, the salts of the compounds (Ic) according to the invention are formed in the first step as intermediates which can be isolated. The acids (Ia) according to the invention are obtained by treating the salts (Ic) with customary inorganic acids. These preferably include mineral acids such as, for example, hydrochloric acid, hydrobromic acid, sulphuric acid or phosphoric acid. In this connection, it has proved advantageous in the preparation of the carboxylic acids (Ia) to acidify the basic reaction mixture from the hydrolysis in a second step without isolating the salts. The acids can then be isolated in a customary manner.

In order to prepare the lactones of the formula (Id) according to the invention, the carboxylic acids (Ia) according to the invention are in general cyclized by customary methods, for example by heating the corresponding acid in inert organic solvents, if appropriate in the presence of molecular sieve.

Suitable solvents in this connection are hydrocarbons such as benzene, toluene, xylene, mineral oil fractions, or tetralin or diglyme or triglyme. Benzene, toluene or xylene are preferably employed. It is also possible to employ mixtures of the solvents mentioned. Hydrocarbons are particularly preferably used, in particular toluene, in the presence of molecular sieve.

The cyclization is in general carried out in a temperature range from −40° C. to +200° C., preferably from −25° C. to +50° C.

The cyclization is in general carried out at normal pressure, but it is also possible to carry out the process at reduced pressure or at elevated pressure (for example in a range from 0.5 to 5 bar).

Moreover, the cyclization can also be carried out in inert organic solvents, with the aid of cyclizing or dehydrating agents. In this connection, carbodiimides are preferably used as dehydrating agents. N,N'-Dicyclohexylcarbodiimide paratoluenesulphonate, N-cyclohexyl-N'-[2-(N''-methylmorpholinium)ethyl]carbodiimide or N-(3-dimethylaminopropyl)-N'-ethylcarbodiimide hydrochloride are preferably employed as carbodiimides.

Suitable solvents in this connection are the customary organic solvents. These preferably include ethers such as diethyl ether, tetrahydrofuran or dioxane, or chlorinated hydrocarbons such as methylene chloride, chloroform or carbon tetrachloride, or hydrocarbons such as benzene, toluene, xylene or mineral oil fractions. Chlorinated hydrocarbons such as, for example, methylene chloride, chloroform or carbon tetrachloride, or hydrocarbons such as benzene, toluene, xylene, or mineral oil fractions are particularly preferred. Chlorinated hydrocarbons such as, for example, methylene chloride, chloroform or carbon tetrachloride are very particularly preferably employed.

The cyclization is in general carried out in a temperature range from 0° C. to +80° C., preferably from +10° C. to +50° C.

When carrying out the cyclization, it has proved advantageous to employ the cyclization method with the aid of carbodiimides as dehydrating agents.

The resolution of the isomers into the stereoisomerically uniform constituents is in general carried out by customary methods such as are described, for example, by E. L. Eliel, Stereochemistry of Carbon Compounds, McGraw Hill, 1962. In this connection, the separation of the isomers in the racemic ester step is preferred. In this connection, the racemic mixture of the trans-lactones (VII) is particularly preferably converted by treating either with D-(+)- or L-(−)-α-methylbenzylamine by customary methods into the diastereomeric dihydroxyamides (Ie)

(Ie)

described above is dependent on the configuration of the starting substances.

The resolution of the isomers is intended to be illustrated by way of example in the following scheme:

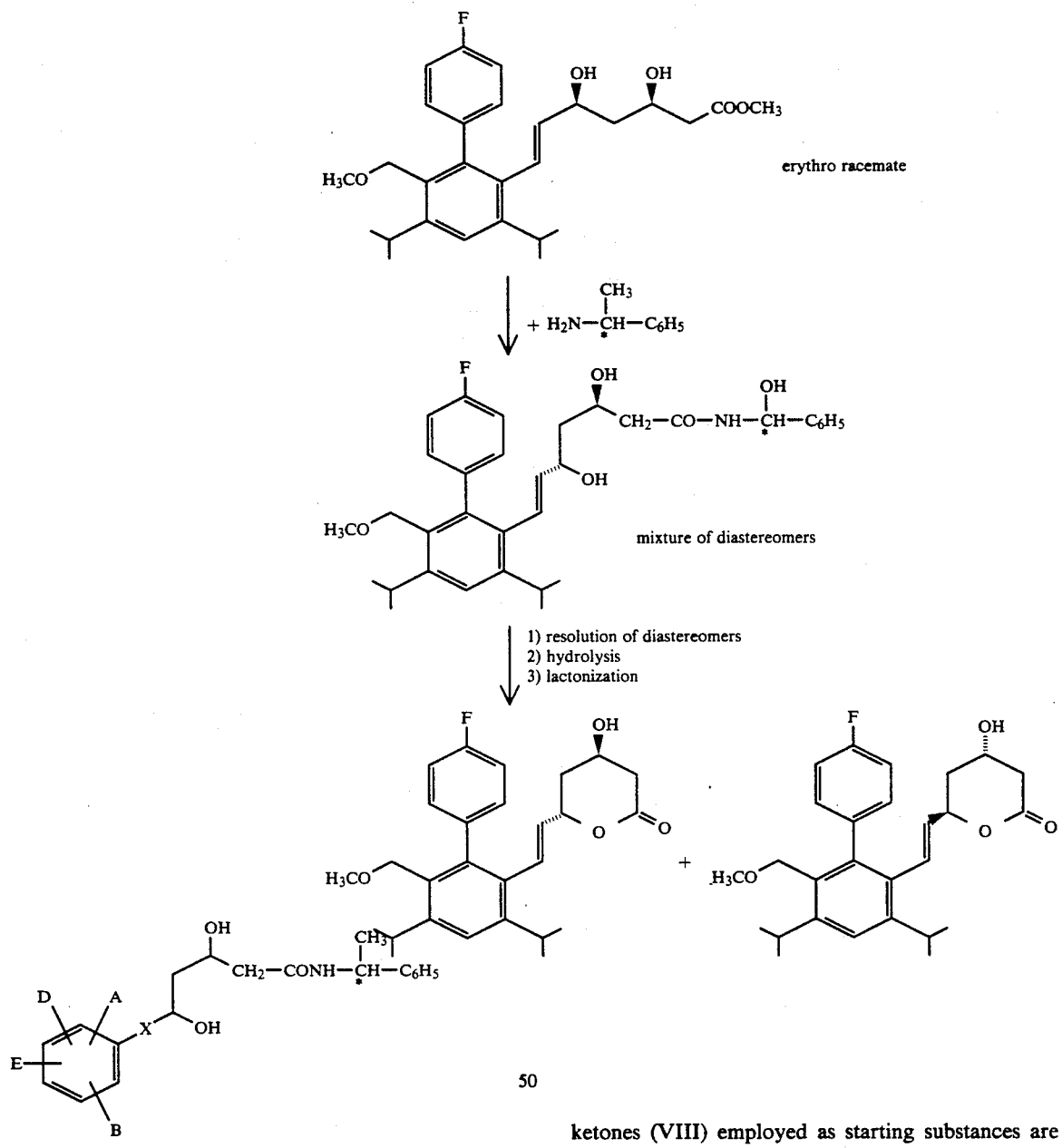

which can then be resolved into the individual diastereomers as is customary by chromatography or crystallization. Subsequent hydrolysis of the pure diastereomeric amides by customary methods, for example by treating the diastereomeric amides with inorganic bases such as sodium hydroxide or potassium hydroxide in water and/or organic solvents such as alcohols, for example methanol, ethanol, propanol or isopropanol, give the corresponding enantiomerically pure dihydroxy acids (Ia) which can be converted into the enantiomerically pure lactones as described above by cyclization. In general, it is true for the preparation of the compounds of the general formula (I) according to the invention in enantiomerically pure form that the configuration of the final products according to the method ketones (VIII) employed as starting substances are new.

A process for the preparation of the ketones of the general formula (VIII) according to the invention

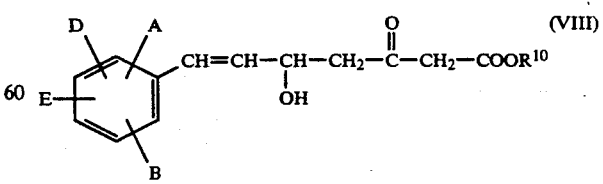

in which

A, B, D, E and $R^{10}$ have the abovementioned meanings, has been found, which is characterized in that aldehydes of the general formula (IX)

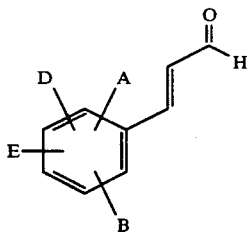 (IX)

in which

A, B, D and E have the abovementioned meanings, are reacted in inert solvents with acetoacetic acid esters of the general formula (X)

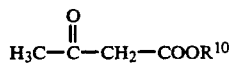 (X)

in which $R^{10}$ has the abovementioned meanings,
in the presence of bases.

The process according to the invention can be illustrated, for example, by the following equation:

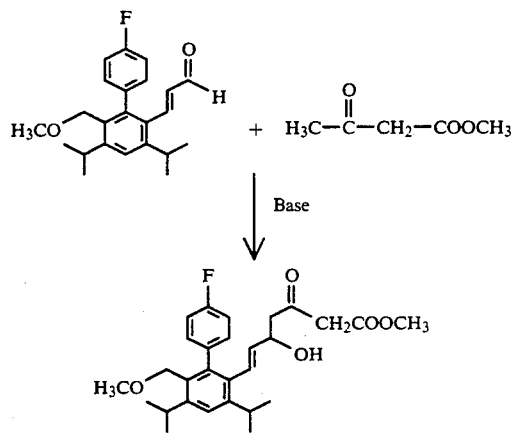

Suitable bases in this connection are the customary strongly basic compounds. These preferably include organolithium compounds such as, for example, n-butyllithium, sec.butyllithium, tert.butyllithium or phenyllithium, or amides such as, for example, lithium diisopropylamide, sodium amide or potassium amide, or lithium hexamethyldisilylamide, or alkali metal hydrides such as sodium hydride or potassium hydride. It is also possible to employ mixtures of the bases mentioned. N-Butyllithium or sodium hydride or a mixture thereof is particularly preferably employed.

Additions of metal halides such as, for example, magnesium chloride, zinc chloride or zinc bromide are possibly advantageous. The addition of zinc halides is particularly preferred.

Suitable solvents in this connection are the customary organic solvents which do not change under the reaction conditions. These preferably include ethers such as diethyl ether, tetrahydrofuran, dioxane or dimethoxyethane, or hydrocarbons such as benzene, toluene, xylene, cyclohexane, hexane or mineral oil fractions. It is also possible to employ mixtures of the solvents mentioned. Ethers such as diethyl ether or tetrahydrofuran are particularly preferably used.

The reaction is in general carried out in a temperature range from −80° C. to +50° C., preferably from −20° C. to room temperature.

The process is in general carried out at normal pressure, but it is also possible to carry out the process at reduced pressure or at elevated pressure, for example in a range from 0.5 to 5 bar.

When carrying out the process, the acetoacetic acid ester is in general employed in an amount from 1 to 2, preferably from 1 to 1.5 moles, relative to 1 mole of the aldehyde.

The acetoacetic acid esters of the formula (XI) employed as starting substances are known or can be prepared by known methods [Beilstein's Handbuch der organischen Chemie (Beilstein's Handbook of Organic Chemistry), III, 632; 438].

Acetoacetic esters which may be mentioned by way of example for the process according to the invention are:

methyl acetoacetate, ethyl acetoacetate, propyl acetoacetate and isopropyl acetoacetate.

The preparation of the aldehydes of the general formula (IX) employed as starting substances is intended to be illustrated by way of example for the substituted biphenyls in the following.

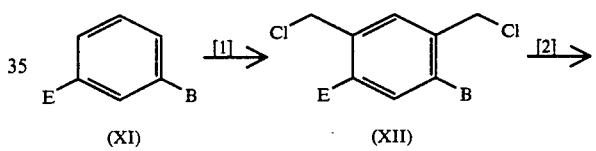

(XI)　　　　　　(XII)

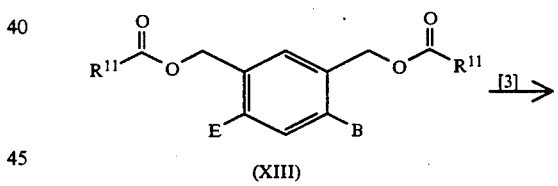

(XIII)

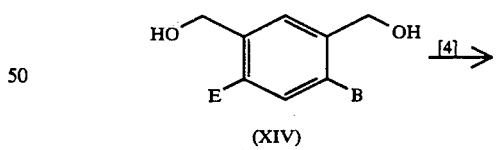

(XIV)

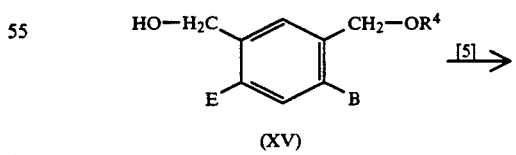

(XV)

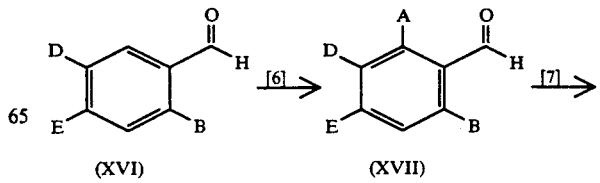

(XVI)　　　　　　(XVII)

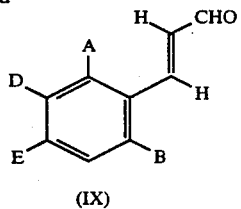

(IX)

The radicals A, B, D, E and $R^4$ of the formulae (XI), (XII), (XIII), (XIV), (XV), (XVI), (XVII) and (IX) have the abovementioned meanings and $R^{11}$ represents a ($C_1$–$C_4$)-alkyl radical.

In this connection, substituted phenyls of the formula (XI) are converted into the bis-(chloromethyl) compounds of the formula (XII) in the first step [1] by known methods [Org. React. 1, 68, T. Sato and T. Takemura, J. Chem. Soc., Perk. Trans II, 1195 (1976)]. The bisacetoxy compounds (XIII), the hydrolysis of which [3] by customary methods yields the bishydroxymethyl compounds (XIV), are obtained by reaction 2] of the compounds of the formula (XII) with, for example, sodium acetate in solvents such as dimethylformamide in a temperature range from +20° C. to +100° C. In a fourth step [4], the bishydroxymethyl compounds of the formula (XIV) can be converted into the hydroxymethyl compounds (XV) by known methods, for example by reaction with alkyl halides in the presence of sodium hydride or potassium hydride in the abovementioned inert solvents, such as, for example, tetrahydrofuran or by reaction with trialkylchlorosilanes in the presence of a base such as, for example, imidazole in solvents such as, for example, dimethylformamide, or by acylation by customary methods. Furthermore, a hydroxymethyl group of the bishydroxyethylene compounds (XIV) can be converted into a leaving group by known methods, for example by reaction with trifluoromethanesulphonic anhydride, thionyl chloride or methanesulphonyl chloride in the presence of a base. The leaving group can then be exchanged for nucleophiles by known methods.

The hydroxymethyl compounds (XV) are oxidized to the aldehydes (XVI) in the fifth step [5] by customary methods. The oxidation can be carried out, for example, with pyridinium chlorochromate, if appropriate in the presence of alumina, in inert solvents such as chlorinated hydrocarbons, preferably methylene chloride, in a temperature range from 0° C. to 60° C., preferably at room temperature, or else with trifluoroacetic acid/dimethyl sulphoxide according to the customary methods of Swern oxidation. In the sixth step [6], the aldehydes (XVII) are synthesized by known methods by introducing the substituent A, which has the abovementioned meaning [compare Shun-Ichi Murahashi, Yoshihiro Tamba, Masaaki Yamamura and Noriaki Yoshimura, J. Org. Chem. 43, 4099 (1978)]. The aldehydes (XVII) are reacted to give the aldehydes (IX) in the seventh step [7]using diethyl 2-(cyclohexylamino)-vinylphosphonate in the presence of sodium hydride in inert solvents such as ethers, for example diethyl ether, tetrahydrofuran or dioxane, preferably in tetrahydrofuran, in a temperature range of −20° C. to +40° C., preferably from −5° C. to room temperature.

The compounds of the general formula (I) according to the invention have useful pharmacological properties and can be employed in medicaments. In particular, they are inhibitors of 3-hydroxy-3-methylglutarylcoenzyme A (HMG-CoA) reductase and, in view of this, inhibitors of cholesterol biosynthesis They can therefore be employed for the treatment of hyperlipoproteinaemia, lipoproteinaemia or atherosclerosis. The active compounds according to the invention additionally cause a lowering of the cholesterol content in the blood.

The enzyme activity determination was carried out as modified by G. C. Ness et al., Archives of Biochemistry and Biophysics 197, 493–499 (1979). Male Rico rats (body weight 300–400 g) were treated for 11 days with Altromin powdered feed, to which 40 g of cholestyramine/kg of feed had been added. After decapitation, the liver was removed from the animals and placed on ice. The livers were comminuted and homogenized 3 times in 3 volumes of 0.1M sucrose, 0.05M KCl, 0.04M $K_xH_y$ phosphate, 0.03M ethylenediaminetetraacetic acid, 0.002M dithiothreitol (SPE) buffer pH 7.2 in a Potter-Elvejem homogenizer. The mixture was then centrifuged for 15 minutes at 15,000 g and the sediment was discarded. The supernatant was sedimented at 100,000 g for 75 minutes. The pellet is taken up in ¼ volumes of SPE buffer, homogenized again and then centrifuged at 100,000 g for 60 minutes. The pellet is taken up using a 5-fold amount of its volume of SPE buffer, homogenized and frozen and stored at −78° C. (=enzyme solution).

For testing, the test compounds (or mevinolin as reference substance) were dissolved in dimethylformamide with the addition of 5 vol.-% of 1N NaOH and, using 10 µl, employed in various concentrations in the enzyme test. The test was started after 20 minutes' preincubation of the compounds with the enzyme at 37° C. The test batch was 0.380 ml and contained 4 µmol of glucose-6-phosphate, 1.1 mg of bovine serum albumin, 2.1 µmol of dithiothreitol, 0.35 µmol of NADP, 1 unit of glucose-6phosphate dehydrogenase, 35 µmol of $K_xH_y$ phosphate pH 7.2, 20 µl of enzyme preparation and 56 nmol of 3xhydroxy-3-methyl-glutaryl coenzyme A (glutaryl-3-$^{14}$C) 100,000 dpm.

After an incubation of 60 minutes at 37° C. the batch was centrifuged and 600 µl of the supernatant was applied to a 0.7×4 cm column packed with a 100–200 mesh 5 chloride (anion exchanger). The column was washed with 2 ml of distilled water and 3 ml of Aquasol was added to the runnings plus washing water and counted in an LKB scintillation counter. $IC_{50}$ values were determined by intrapolation by plotting the percentage inhibition against the concentration of the compound in the test. In order to determine the relative inhibitory potency, the $IC_{50}$ value of the reference substance mevinolin was set at 1 and compared with the simultaneously determined $IC_{50}$ value of the test compound.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration of about 0.5 to 98% by weight, preferably 1% to 90% by weight, of the total mixture, i.e. in amounts which are sufficient in order to achieve the dosage range indicated.

The formulations are prepared, for example, by extending the active compounds using solvents and/or excipients, if appropriate using emulsifiers and/or dispersants, where, for example, in the case of the use of water as a diluent, organic solvents can optionally be used as auxiliary solvents.

Auxiliaries which may be mentioned, for example, are: water, non-toxic organic solvents, such as paraffins (for example mineral oil fractions), vegetable oils (for example groundnut/sesame oil), alcohols (for example: ethyl alcohol, glycerol), excipients, such as, for example, ground natural minerals (for example kaolins, aluminas, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers, alkylsulphonates and arylsulphonates), dispersants (for example lignin-sulphite waste liquors, methylcellulose, starch and polyvinylpyrrolidone) and lubricants (for example magnesium stearate, talc, stearic acid and sodium laurylsulphate).

Administration takes place in a customary manner, preferably orally, parenterally, perlingually or intravenously. In the case of oral administration, tablets may of course also contain additions, such as sodium citrate, calcium carbonate and dicalcium phosphate together with various additives, such as starch, preferably potato starch, gelatin and the like in addition to the excipients mentioned. Furthermore, lubricants, such as magnesium stearate, sodium laurylsulphate and talc can additionally be used for tabletting. In the case of aqueous suspensions, various flavour enhancers or colourants may be added to the active compounds in addition to the abovementioned auxiliaries.

In the case of parenteral administration, solutions of the active compounds may be employed using suitable liquid excipients.

In general, it has proved advantageous on intravenous administration to administer amounts of about 0.001 to 1 mg/kg, preferably about 0.01 to 0.5 mg/kg of body weight to attain effective results, and on oral administration the dosage is about 0.01 to 20 mg/kg, preferably 0.1 to 10 mg/kg of body weight.

In spite of this it may be necessary to deviate from the amounts mentioned, depending on the body weight or the type of application route, on individual behavior towards the medicament, the manner of its formulation and the point in time or interval at which administration takes place.

Thus, in some cases it may be sufficient to manage with less than the minimum amount previously mentioned, whereas in other cases the upper limit mentioned must be exceeded. In the case of the administration of larger amounts, it may be advisable to divide these into a number of individual doses over the day.

PREPARATION EXAMPLES

Example 1

2,4-Bis-(chloromethyl)-1,5-diisopropylbenzene

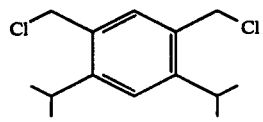

55 ml (0.46 mol) of tin tetrachloride are added dropwise with cooling in an ice bath (exothermic reaction) to a solution of 230 ml (2.43 mol) of chloromethyl ethyl ether and 197 g (1.22 mol) of 1,3-diisopropylbenzene in 600 ml of carbon tetrachloride and the mixture is stirred at 0° C. for 1 h. After stirring overnight at +25° C., 142 g (1.5 mol) of chloromethyl ethyl ether and 74 ml (0.46 mol) of tin tetrachloride are again added dropwise at 0° C. and the mixture is stirred overnight at +25° C. The reaction mixture is added to ice/hydrochloric acid, and the organic phase is separated off, washed with water and dried using sodium sulphate. After concentrating, the residue is taken up with petroleum ether, filtered through 1 kg of silica gel (230–400 mesh) and distilled in a high vacuum.

B.p.: 133°–139° C./1.2 Torr.

Yield: 89.9 g (28% of theory).

$^1$H-NMR (CDCl$_3$): δ (ppm)=1.2 (d, 12H); 3.2 (sept., 2H); 4.55 (s, 4H); 7.2 (2s; 2H).

EXAMPLE 2

2,4-Bis-(acetoxymethyl)-1,5-diisopropylbenzene

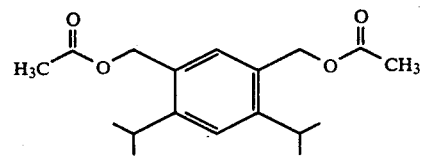

40.0 g (154 mmol) of the compound from Example 1 and 22.7 g (277 mmol) of sodium acetate are heated overnight at 80° C. in 200 ml of dimethylformamide. After distilling off the solvent, the residue is taken up with petroleum ether, washed with water and dried using sodium sulphate.

Crude yield: 40.2 g (85% of theory).

$^1$H-NMR (CDCl$_3$): δ (ppm)=1.25 (d, 12H); 2.1 (s, 6H); 3.15 (sept, 2H); 5.15 (s, 4H); 7.3 (2s, 2H).

EXAMPLE 3

2,4-Bis-(hydroxymethyl)-1,5-diisopropylbenzene

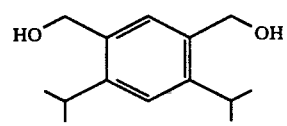

40.2 g (131 mmol) of the compound from Example 2 are stirred at 50° C. for 3 h with 16.1 g (0.3 mol) of potassium hydroxide in 200 ml of methanol. After distilling off the solvent, the residue is taken up in ether, washed with water, dried using sodium sulphate and recrystallized from ethyl acetate/petroleum ether.

Yield: 17.3 g (59.5% of theory).

M.p.: 102°–104° C.

$^1$H-NMR (CDCl$_3$): δ (ppm)=1.25 (d, 12H); 1.7 (s, 2H); 3.25 (sep., 2H); 4.7 (s, 4H); 7.3 (2s, 2H).

EXAMPLE 4

2-Hydroxymethyl-4-methoxymethyl-1,5-diisopropylbenzene

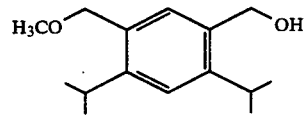

31.5 g (0.14 mol) of the compound from Example 3 and 9.6 ml (0.15 mol) of methyl iodide are added under a nitrogen atmosphere to 8.9 g (0.3 mol) of sodium hydride (80% strength in paraffin oil) in 500 ml of tetrahydrofuran. After stirring for 2 h at 80° C., the mixture is cautiously hydrolyzed using 30 ml of dilute hydrochloric acid, the solvent is distilled off, and the residue is taken up in methylene chloride, washed with water, dried and chromatographed on silica gel (230-400 mesh, ethyl acetate/petroleum ether 1:2).

Yield: 15.7 g (47.5% of theory) and 7.7 g of educt (24.8% of theory).

$^1$H-NMR (CDCl$_3$): δ (ppm)=1.25 (d, 12H); 1.45 (tr, 1H); 3.2 (m, 2H); 3.4 (s, 3H); 4.45 (s, 2H); 4.7 (d, 2H); 7.25 (s, 2H).

EXAMPLE 5

2,4-Diisopropyl-5-ethoxymethyl-benzaldehyde

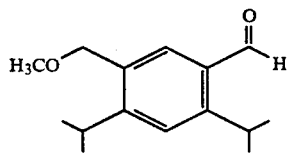

17.2 g (80 mmol) of pyridinium chlorochromate are added to a solution of 15.7 g (66.5 mmol) of the compound from Example 4 in 300 ml of methylene chloride, the mixture is stirred overnight at room temperature, filtered with suction through kieselgur, washed with 200 ml of methylene chloride, and dried using sodium sulphate.

Yield: 10.4 g (66.8% of theory).

$^1$H-NMR (CDCl$_3$): δ (ppm)=1.30 (m, 12H); 3.25 (sept. 1H); 3.4 (s, 3H); 4.0 (sept., 1H); 4.56 (s, 2H); 7.4 (s, 1H); 7.75 (s, 1H); 10.3 (s, 1H).

EXAMPLE 6

N-[2,4-Diisopropyl-5-methoxymethyl-benzal]-phenylamine

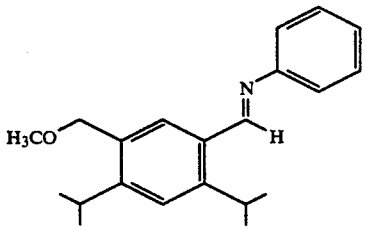

A solution of 10.36 g (44.3 mmol) of the compound from Example 5, 4.06 g (44.6 mmol) of freshly distilled aniline and 0.3 g of p-toluenesulphonic acid in 370 ml of toluene is heated under reflux for 1.5 h in a water separator (molecular sieve 4 Å), diluted with ethyl acetate after cooling to room temperature, washed with saturated sodium hydrogencarbonate solution and water, dried using sodium sulphate and concentrated in vacuo.

Yield: 13.26 g of oil (98.5% of theory).

$^1$H-NMR (CDCl$_3$) δ (ppm)=1.3 (m, 12H); 3.3 (sept., 1H); 3.4 (s, 3H); 3.65 (sept, 1H); 4.55 (s, 2H); 7.1–7.4 (m, 7H); 8.0 (s, 1H); 8.8 (s, 1H).

EXAMPLE 7

Bis-{2,4-diisopropyl-5-methoxymethyl-1-[(phenylimino)methyl]phenyl-C,N}-dipalladium

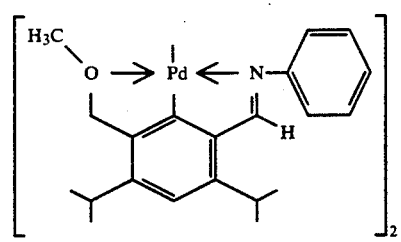

A mixture of 13.25 g (42.75 mmol) of the compound from Example 6 and 9.60 g (42.75 mmol) of palladium-(II) acetate in 200 ml of glacial acetic acid are heated under reflux for 1 h. After cooling to room temperature, the reaction mixture is poured into 800 ml of water, and the precipitated solid is filtered off with suction and washed with water. The aqueous solution is concentrated to dryness, taken up in ethyl acetate, washed with sodium hydrogencarbonate solution and sodium chloride solution, dried using sodium sulphate and, after concentrating, stirred with 100 ml of petroleum ether-/ethyl acetate 1:1. The precipitated product is dried in vacuo over potassium hydroxide.

Yield: 7.1 g (39% of theory).

$^1$H-NMR (CDCl$_3$): δ (ppm)=1.3 (m, 12H); 2.7 (sept, 1H); 3.2 (sept, 1H); 3.95 (s, 3H); 5.8 (s, 2H); 6.85 (s, 1H); 7.25–7.6 (m, 5H); 8.15 (s, 1H).

EXAMPLE 8

1,1,-Biphenyl-3,5-diisopropyl-4,-fluoro-6-methoxymethyl-2-carbaldehyde

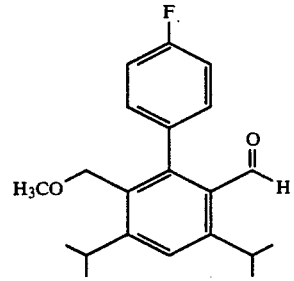

A solution of 3.5 g (4.1 mmol) of the compound from Example 7 and 8.35 g (31.9 mmol) of triphenylphosphine in 80 ml of benzene is stirred at room temperature under a nitrogen atmosphere for 30 min. A solution of 4-fluorophenylmagnesium bromide (prepared from 0.845 g (34.7 mmol) of magnesium and 3.94 ml (35.2 mmol) of 4-bromofluorobenzene in 30 ml of ether) is added to this solution and the mixture is stirred overnight. The latter is hydrolyzed with ice cooling using 24 ml of 6N hydrochloric acid, stirred at room temperature for 1 h, the precipitated solid is filtered off with suction, and the filtrate is diluted using ether, washed with sodium chloride solution and dried using sodium sulphate. 11.21 g of oil are obtained after concentrating. Chromatography on silica gel (230–400 mesh, ethyl acetate/petroleum ether 1:20) gives 1.05 g of crude product, repeated chromatography on silica gel (70–230 mesh, ethyl acetate/petroleum ether 1:80) gives 670 mg of solid.

Yield: 50% of theory.
Melting point: 62°-70° C.
$^1$H-NMR (CDCl$_3$) δ (ppm)=1.3 (m, 12H); 3.15 (s, 3H); 3.35 (sept, 1H); 3.9 (sept, 1H); 4.05 (s, 2H); 7.05-7.3 (m, 4H); 7.45 (s, 1H); 9.7 (s, 1H).

EXAMPLE 9

(E)-3-[1,1'-Biphenyl-3,5-diisopropyl-4'-fluoro-6-methoxymethyl-2-yl]-prop-2-enal

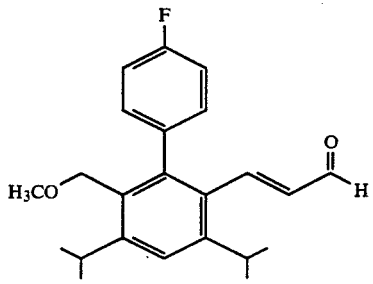

728 mg (2.79 mmol) of diethyl 2-(cyclohexylamino)-vinylphosphonate, dissolved in 6 ml of dry tetrahydrofuran, are added dropwise under nitrogen to a suspension of 53 mg (2.23 mmol) of sodium hydride in 6 ml of dry tetrahydrofuran at −5° C. After 30 min, 610 mg (1.86 mmol) of the compound from Example 8 in 15 ml of dry tetrahydrofuran are added dropwise at the same temperature and the mixture is heated to reflux for 30 min. After cooling to room temperature, the batch is added to 200 ml of ice-cold water and extracted 3 times using 100 ml of ethyl acetate each time. The combined organic phases are washed with satured sodium chloride solution and dried over sodium sulphate. After concentrating in vacuo, the residue is taken up in 5 ml of toluene, a solution of 0.9 g (7 mol) of oxalic acid dihydrate in 12 ml of water is added and the mixture is heated to reflux for 90 min. After cooling to room temperature, the phases are separated, and the organic phase is washed with saturated sodium chloride solution, dried over sodium sulphate and concentrated in vacuo. The residue is chromatographed on silica gel (230-400 mesh, ethyl acetate/petroleum ether 1:10).

Yield: 480 mg (72.8% of theory).
Melting point: 94°-96° C.
$^1$H-NMR (CDCl$_3$): δ (ppm)=1.25 (d, 6H); 1.35 (d, 6H); 3.15 (s, 3H); 3.2 (sept., 1H); 3.35 (sept., 1H); 4.05 (s, 2H); 5.95 (dd, 1H); 7.0-7.3 (m, 5H); 7.4 (s, 1H); 9.35 (d, 1H).

EXAMPLE 10

Methyl (E)-7-[1,1'-biphenyl-3,5-diisopropyl-4'-fluoro-6-methoxymethyl-2-yl]-5-hydroxy-3-oxo-hept-6-enoate

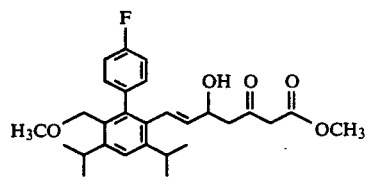

0.31 ml (2.84 mmol) of methyl acetate is added dropwise under nitrogen to a suspension of 70 mg (2.92 mmol) of sodium hydride in 3 ml of dry tetrahydrofuran at −5° C. After 15 min, 1.81 ml (2.89 mmol) of 15% strength n-butyllithium in n-hexane are added dropwise at the same temperature and the mixture is stirred for 15 min. 480 mg (1.35 mmol) of the compound from Example 9 dissolved in 8 ml of dry tetrahydrofuran are then added dropwise and the mixture is stirred at −5° C. for 30 min. The reaction solution is cautiously diluted using 100 ml of saturated aqueous ammonium chloride solution and the mixture is extracted three times using 100 ml of ether each time. The combined organic phases are washed twice with saturated sodium hydrogencarbonate solution and once with saturated sodium chloride solution, dried over sodium sulphate and concentrated in vacuo.

Crude yield: 740 mg (100% of theory).
$^1$H-NMR (CDCl$_3$): δ (ppm)=1.25 (m, 12H); 2.4 (m, 2H); 3.15 (s, 3H); 3.3 (m, 2H); 3.45 (s, 2H); 3.75 (s, 3H); 4.05 (s, 2H); 4.45 (m, 1H); 5.2 (dd, 1H); 6.35 (d, 1H); 7.0-7.25 (m, 4H); 7.3 (s, 1H).

EXAMPLE 11

Methyl erythro-(E)-7-[1,1'-biphenyl-3,5-diisopropyl-4'-fluoro-6-methoxymethyl-2-yl]-3,5-dihydroxy-hept-6-enoate

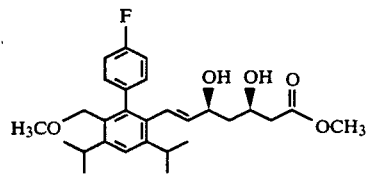

1.7 ml (1.7 mmol) of 1M triethylborane solution in tetrahydrofuran are added at room temperature to a solution of 680 mg (1.45 mmol) of the compound from Example 10 in 13 ml of dry tetrahydrofuran, air is passed through the solution for 5 min and the mixture is cooled to an internal temperature of −30° C. 66 mg (1.7 mmol) of sodium borohydride and, slowly, 1.2 ml of methanol are added, the mixture is stirred at −30° C. for 30 min and a mixture of 4.7 ml of 30% strength hydrogen peroxide and 10 ml of water is then added. The temperature is allowed to increase to 0° C. during the course of this and the mixture is stirred for a further 30 min. The mixture is extracted three times using 70 ml of ethyl acetate each time, and the combined organic phases are washed once each with 10% strength potassium iodide solution, 10% strength sodium thiosulphate solution, saturated sodium hydrogencarbonate solution and saturated sodium chloride solution, dried over sodium sulphate and concentrated in vacuo. The residue is chromatographed on a column (silica gel 230-400 mesh, ethyl acetate/petroleum ether 1:2).

Yield: 480 mg (70.5% of theory).
$^1$H-NMR (CDCl$_3$): δ (ppm)=1.25 (m, 12H); 1.4 (m, 2H); 2.4 (m, 2H); 3.1 (s, 3H); 3.15 (m, 1H); 3.3 (m, 1H); 3.7 (s, 3H); 4.05 (m, 3H); 4.25 (m, 1H); 5.2 (dd, 1H); 6.3 (d, 1H); 6.95-7.15 (m, 4H); 7.3 (s, 1H).

EXAMPLE 12

2,4-Bis-(acetoxymethyl)-1,5-dimethylbenzene

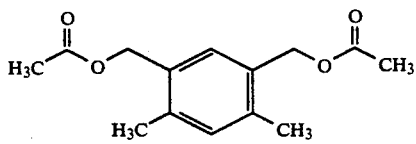

Analogously to Example 2, 554.7 g of crude oil are obtained from 500 g (80% pure, 1.97 mol) of 2,4-bis-(chloromethyl)-1,5-dimethylbenzene.
Yield: 100% of theory.
$^1$H-NMR (CDCl$_3$): δ (ppm)=2.1 (s, 6H); 2.3 (s, 6H); 5.1 (s, 4H); 7.05 (s, 1H); 7.3 (s, 1H).

EXAMPLE 13

2,4-Bis-(hydroxymethyl)-1,5-dimethylbenzene

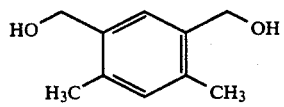

Analogously to Example 3, 234.4 g of solid are obtained from 554.7 g (1.97 mol) of the compound from Example 12.
Yield: 7.16% of theory.
$^1$H-NMR (CDCl$_3$): δ (ppm)=2.3 (s, 6H); 4.65 (s, 4H); 6.95 (s, 1H); 7.35 (s, 1H).

EXAMPLE 14

2-tert.Butyldimethylsilyloxymethyl-4-hydroxymethyl-1,5-dimethylbenzene

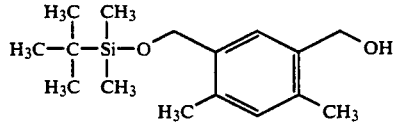

212.9 g (1.41 mol) of tert.butyldimethylsilyl chloride, 105.7 g (1.55 mol) of imidazole and 0.05 g of 4-dimethylaminopyridine are added at room temperature to a solution of 234.2 g (1.41 mol) of the compound from Example 13 in 1.8 l of dimethylformamide. The mixture is stirred overnight at room temperature, the solvent is distilled off on a rotary evaporator, the residue is taken up using ethyl acetate, the mixture is filtered and the filter residue is washed with ethyl acetate. The combined ethyl acetate phases are washed with dilute hydrochloric acid, saturated sodium hydrogencarbonate solution and saturated sodium chloride solution, dried over sodium sulphate and concentrated in vacuo.
Yield: 314.4 g (78.8% of theory).

EXAMPLE 15

2-Hydroxymethyl-4-methoxymethyl-1,5-dimethylbenzene

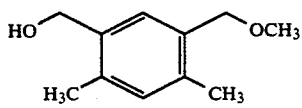

43.7 g (1.46 mol) of sodium hydride (80% strength in paraffin oil) and 77.4 ml (1.23 mol) of methyl iodide are added under a nitrogen atmosphere at 0° C. to a solution of 314.4 g (1.12 mol) of the compound from Example 14 in 2 l of dry tetrahydrofuran and the mixture is stirred overnight at room temperature. The mixture is hydrolysed cautiously with ice cooling using 100 ml of water and concentrated in vacuo, and the residue is washed with ethyl acetate. The ethyl acetate phase is dried using sodium sulphate and concentrated in vacuo. The residue is distilled: b.p. 105°–160° C./0.9 mm 199.9 g.

The distillate (199.9 g, 0.69 mol) is stirred overnight at 25° C. with 800 ml of a 1 molar tetrabutylammonium fluoride solution in tetrahydrofuran and concentrated in vacuo, and the residue is taken up using ethyl acetate and washed three times using 500 ml of 10% strength sulphuric acid each time, twice using saturated sodium hydrogencarbonate solution and water, dried using sodium sulphate and concentrated in vacuo. The distillation of the residue (120.7 g) gives 76.4 g of product at 90°–130° C./0.5 mm.
Yield: 37.8% of theory.
$^1$H-NMR (CDCl$_3$): δ (ppm)=2.3 (2s, 6H); 3.4 (s, 3H);, 4.4 (s, 2H); 4.65 (s, 2H); 7.0 (s, 1H); 7.3 (s, 1).

EXAMPLE 16

2,4-Dimethyl-5-methoxymethyl-benzaldehyde

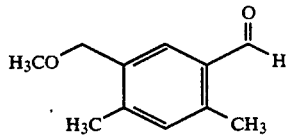

Analogously to Example 5, 25 g of oil are obtained from 30 g (166 mmol) of the compound from Example 15.
Yield: 84.5% of theory.
$^1$H-NMR (CDCl$_3$): δ (ppm)=2.35 (s, 3H); 2.65 (s, 3H); 3.4 (s, 3H); 4.5 (s, 2H); 7.05 (s, 1H); 7.75 (s, 1H); 10.2 (s, 1H).

EXAMPLE 17

N-[2,4-Dimethyl-5-methoxymethyl-benzal]-phenylamine

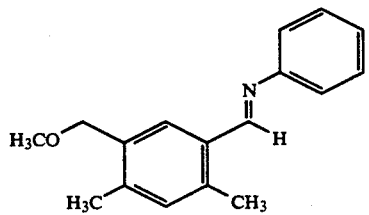

Analogously to Example 6, 21.22 g of crude product are obtained from 16.4 g (90 mmol) of the compound from Example 16.
Yield: 93% of theory.

EXAMPLE 18

Bis-{2,4-dimethyl-5-methoxymethyl-1-[(phenylimino)-methyl]phenyl-C,N}-dipalladium

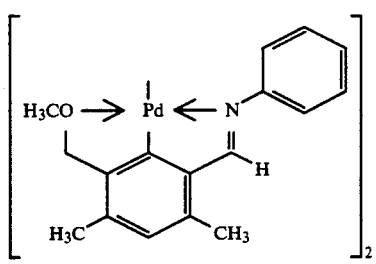

Analogously to Example 7, 11.36 g of solid are obtained from 21.2 g (83.7 mmol) of the compound from Example 17 after dissolving the crude product in a little acetone and precipitating with ether.
Yield: 28.4%.

EXAMPLE 19

1,1'-Biphenyl-3,5-dimethyl-4'-fluoro-6-methoxymethyl-2-carbaldehyde

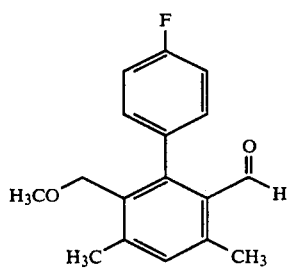

Analogously to Example 8, 2.29 g of product are obtained from 8 g (16.9 mmol) of the compound from Example 18.
Yield: 24.8% of theory.
$^1$H-NMR (CDCl$_3$) δ (ppm)=2.5 (s, 3H); 2.6 (s, 3H); 3.2 (s, 3H); 4.05 (s, 2H); 7.1–7.3 (m, 5H); 9.7 (s, 1H).

EXAMPLE 20

(E)-2-[1,1'-Biphenyl-3,5-dimethyl-4'-fluoro-6-methoxymethyl-2-yl]prop-2-enal

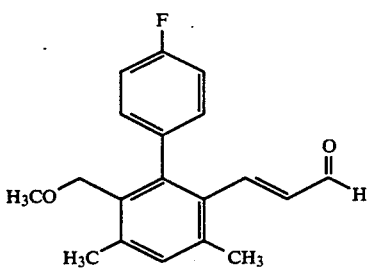

Analogously to Example 9, 2.55 g of crude product are obtained from 2.29 g (8.42 mmol) of the compound from Example 19.
Yield: 100% of theory.
$^1$H-NMR (CDCl$_3$): δ (ppm)=2.4 (2s, 6H), 3.2 (s, 3H); 4.0 (s, 2H); 6.1 (dd, 1H); 7.0–7.3 (m, 6H); 9.35 (d, 1H).

EXAMPLE 21

Methyl (E)-7-[1,1'-biphenyl-3,5-dimethyl-4'-fluoro-6-methoxymethyl-2-yl]-5-hydroxy-3-oxo-hept-6-enoate

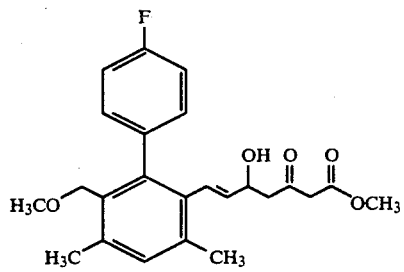

Analogously to Example 10, 3.38 g of crude product are obtained from 2.55 g (8.4 mmol) of the compound from Example 20.
Yield: 95.4% of theory.

EXAMPLE 22

Methyl erythro-(E)-7-[1,1'-biphenyl-3,5-dimethyl-4'-fluoro-6-methoxymethyl-2-yl]-3,5-dihydroxy-hept-6-enoate

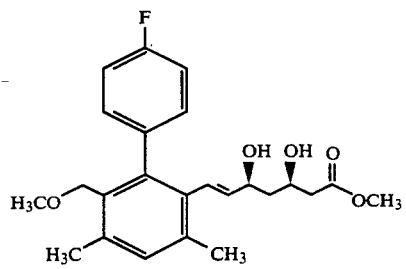

Analogously to Example 11, 920 mg of oil are obtained from 3.38 g (8.1 mmol) of the compound from Example 21.
Yield: 27% of theory. $^1$NMR (CDCl$_3$): δ (ppm)=1.4 (m, 2H); 2.3 (s, 3H); 2.35 (s, 3H); 2.4 (m, 2H); 3.2 (s, 3H); 3.7 (s, 3H); 4.05 (s, 2H); 4.1 (m, 1H); 4.25 (m, 1H); 5.3 (dd, 1H); 6.2 (d, 1H); 6.95–7.2 (m, 5H).

It is understood that the specification and examples are illustrative but not limitative of the present invention and that other embodiments within the spirit and scope of the invention will suggest themselves to those skilled in the art.

We claim:
1. A substituted biphenyl of the general formula

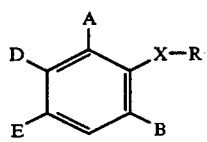

in which
A—represents phenyl which is optionally monosubstituted to trisubstituted by identical or different C$_1$-C$_4$-alkyl or fluorine,
B—represents cyclopropyl or C$_1$-C$_4$-alkyl,
D and E—are identical or different and each represents cyclopropyl, or
straight-chain or branched $C_1$-$C_6$-alkyl which is optionally substituted by a group of the formula

—$OR^4$, wherein
$R^4$—represents hydrogen or $C_1$-$C_4$-alkyl,
X—represents a group —CH=CH—, and
R—denotes a group of the formula

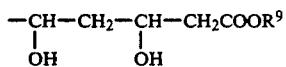

wherein
$R^9$—represents hydrogen, $C_1$-$C_4$-alkyl, benzyl or denotes a sodium, potassium, magnesium or ammonium ion.

2. A compound according to claim 1, wherein such compound is methyl erythro-(E)-7-[1,1'-biphenyl-3,5-diisopropyl-4'-fluoro-6-methoxymethyl-2-yl]-3,5-dihydroxy-hept-6-enoate of the formula

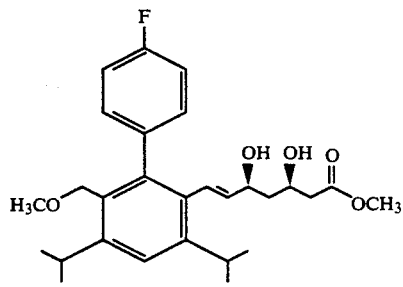

of a salt thereof.

3. A compound according to claim 1, wherein such compound is methyl erythro-(E)-7-[1,1'-biphenyl-3,5-dimethyl-4'-fluoro-6-methoxymethyl-2-yl]-3,5-dihydroxy-hept-6-enoate of the formula

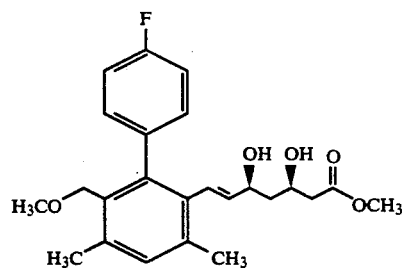

or a salt thereof.

4. An HMG-CoA reductase inhibiting composition comprising an amount effective therefor of a compound or salt according to claim 1 and a diluent.

5. A unit dose of a composition according to claim 1 in the form of a tablet, capsule or ampoule.

6. A method of inhibiting HMG-CoA reductase in a patient in need thereof which comprises administering to such patient an amount effective therefor of a compound or salt according to claim 1.

7. The method according to claim 6, wherein such compound is
methyl erythro-(E)-7-[1,1'-biphenyl-3,5-diisopropyl-4'-fluoro-6-methoxymethyl-2-yl]-3,5-dihydroxy-hept-6-enoate, or
methyl erythro-(E)-7-[1,1'-biphenyl-3,5-dimethyl-4'-fluoro-6-methoxymethyl-2-yl]-3,5-dihydroxy-hept-6-enoate.

* * * * *